(12) United States Patent
Bourdillon et al.

(10) Patent No.: US 10,813,982 B2
(45) Date of Patent: Oct. 27, 2020

(54) COMPOSITION COMPRISING AN OXIDOREDUCTASE ENZYME AND ITS ANTIBACTERIAL USE

(71) Applicant: SYSTAGENIX WOUND MANAGEMENT, LIMITED, West Sussex (GB)

(72) Inventors: Katie Bourdillon, Gargrave (GB); Matthew Westmoreland, Gargrave (GB); Sophie Regan, Gargrave (GB)

( * ) Notice: Subject to any disclaimer, the term of this patent is extended or adjusted under 35 U.S.C. 154(b) by 173 days.

(21) Appl. No.: 15/768,528

(22) PCT Filed: Oct. 14, 2016

(86) PCT No.: PCT/EP2016/074817
§ 371 (c)(1),
(2) Date: Apr. 13, 2018

(87) PCT Pub. No.: WO2017/064311
PCT Pub. Date: Apr. 20, 2017

(65) Prior Publication Data
US 2018/0303912 A1   Oct. 25, 2018

(30) Foreign Application Priority Data
Oct. 16, 2015  (GB) .................................. 1518348.6

(51) Int. Cl.
| | | |
|---|---|---|
| *A61K 38/44* | (2006.01) | |
| *A61P 31/04* | (2006.01) | |
| *A61K 9/00* | (2006.01) | |
| *A61K 31/7004* | (2006.01) | |
| *A61K 9/70* | (2006.01) | |

(52) U.S. Cl.
CPC .......... *A61K 38/443* (2013.01); *A61K 9/0014* (2013.01); *A61K 31/7004* (2013.01); *A61K 38/44* (2013.01); *A61P 31/04* (2018.01); *A61K 9/7092* (2013.01); *C12Y 101/03004* (2013.01)

(58) Field of Classification Search
None
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(Continued)

*Primary Examiner* — Heidi Reese
(74) *Attorney, Agent, or Firm* — Foley & Lardner LLP

(57) ABSTRACT

A composition comprising an oxidoreductase enzyme and a substrate for the enzyme for use in treating or preventing biofilm formation by a population of pathogenic bacteria. The composition can be incorporated into a wound dressing for use in promoting wound healing.

11 Claims, 1 Drawing Sheet

(56) References Cited

U.S. PATENT DOCUMENTS

| | | | |
|---|---|---|---|
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kelt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewell |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 2510944 A1 * | 10/2012 | A61K 33/18 |
| EP | 2510944 A1 | 10/2012 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 01/93875 A1 | 12/2001 | |
| WO | 2009/009156 A2 | 1/2009 | |

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

(56) References Cited

OTHER PUBLICATIONS

Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen,". British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report & Written Opinion in International Application No. PCT/EP2016/074817 dated Dec. 21, 2016 (10 pages).

\* cited by examiner

COMPOSITION COMPRISING AN OXIDOREDUCTASE ENZYME AND ITS ANTIBACTERIAL USE

CROSS-REFERENCE TO RELATED APPLICATIONS

The present application is a U.S. National Phase Application under 35 U.S.C. § 371 of International Application No. PCT/EP2016/074817, filed on Oct. 14, 2016, which claims the benefit of GB Application No. 1518348.6, filed on Oct. 16, 2015, which are each incorporated herein by reference in their entireties.

The present invention relates to compositions useful in the treatment of pathogenic bacterial biofilms.

Biofilms are collections of microorganisms which adhere to surfaces, surrounding themselves with secreted polymers and forming three dimensional microbial communities with coordinated multi-cellular behaviour. The ability of bacteria to form these complex communities is believed to impede activity of host defences and treatments against pathogens, with biofilm populations often displaying a tolerance to antimicrobial treatment.

Bacterial biofilms are known to be associated with a variety of medical conditions including dental caries, *Pseudomonas* infection in the lungs of cystic fibrosis patients and endocarditis due to biofilms growing on artificial heart valves. Increasing evidence indicates that biofilms may also contribute to delayed wound healing, particularly in chronic wounds.

It has been estimated that 60-80 percent of microbial infections in the body are caused by bacteria growing as a biofilm, as opposed to free-floating bacteria.

Biofilms can grow on most surfaces including wounds and are thought to induce inflammation and therefore delay wound healing.

It is well established that a composition which has demonstrated antimicrobial efficacy against vegetative bacteria is often not also effective against biofilms formed by the same bacteria. This is true for both antibiotics and broad spectrum antiseptics such as silver, iodine and honey (Saginur et al. 2006; Antimicrob Agents and Chemother 50(1) 55-61).

There is a continued requirement for effective treatments of pathogenic bacterial biofilms.

Compositions comprising an oxidoreductase enzyme and a substrate for the enzyme, and methods or uses involving such compositions, are described herein. A composition comprising an oxidoreductase enzyme and a substrate for the enzyme may be used to treat or prevent biofilm formation by a population of pathogenic bacteria, e.g., to reduce or reverse formation of a pathogenic bacterial biofilm on a surface, or to remove a pathogenic bacterial biofilm from a surface. Accordingly, methods of treating or preventing biofilm formation by administration or application of such a composition, are described. Use of the compositions may be antiseptic, to treat or prevent biofilm formation in or on a patient (e.g., at the site of a wound) or disinfectant, to treat or prevent biofilm formation in or on an inanimate object (e.g., on a medical device).

In one aspect, a composition comprising an oxidoreductase enzyme and a substrate for the enzyme for use in treating or preventing biofilm formation by a population of pathogenic bacteria in or on a patient is disclosed.

Biofilm formation includes establishment of a biofilm and/or biofilm-like growth.

The composition comprises a therapeutically effective amount of the enzyme and substrate for treating or preventing biofilm formation.

In one embodiment, the composition does not comprise lactoperoxidase.

The composition can consist of an oxidoreductase enzyme, a substrate for the enzyme and a pharmaceutically acceptable carrier.

In use, the composition can be hydrated, for example by wound exudate, and this assists the process of the enzyme metabolising the enzyme substrate to produce hydrogen peroxide. For example, glucose oxidase metabolises glucose producing hydrogen peroxide.

Usually the methods and uses described herein will comprise applying or administering both the enzyme and its substrate. However, where an appropriate substrate for the enzyme is present or expected to be present at the site to be treated, the enzyme may be applied or administered alone, where it may combine with its substrate at the application site or surface being treated.

The composition treats biofilm formation by causing a reduction in biofilm formation which would be considered a statistically significant reduction relative to untreated biofilm by a skilled person. A significant reduction is a I-reduction in biofilm total viable count of at least 1 $\log_{10}$ unit. The reduction in biofilm formation could also be a I-reduction in biofilm total viable count of at least 2, at least 3, at least 4 or at least 5 $\log_{10}$ units.

In a preferred embodiment, the oxidoreductase enzyme is glucose oxidase and the substrate is glucose. The glucose can be provided as honey. The glucose content of the honey can be over 20 g per 100 g, including 25 g-40 g per 100 g.

In a further preferred embodiment, the oxidoreductase enzyme is fructose oxidase and the substrate is fructose. In a further preferred embodiment, the oxidoreductase enzyme is hexose oxidase and the substrate is a hexose sugar. In a further preferred embodiment, the oxidoreductase enzyme is cholesterol oxidase and the substrate is cholesterol. In a further preferred embodiment, the oxidoreductase enzyme is galactose oxidase and the substrate is galactose. In a further preferred embodiment, the oxidoreductase enzyme is pyranose oxidase and the substrate is pyranose. In a further preferred embodiment, the oxidoreductase enzyme is choline oxidase and the substrate is choline. In a further preferred embodiment, the oxidoreductase enzyme is pyruvate oxidase and the substrate is pyruvate. In a further preferred embodiment, the oxidoreductase enzyme is glycollate oxidase and the substrate is glycollate.

A mixture of oxidoreductase enzymes and their corresponding substrates can also be used. For example, glucose oxidase, glucose, fructose oxidase and fructose can be used.

The composition can be a substantially neutral pH.

In a further embodiment, the pH can be 4.5-6.5, including pH 4.5 to 5.5.

The composition can be combined with other antibacterial treatments, such as ionic silver, iodine, antibiotics, Prontosan®, PHMB, chlorhexidine, copper or surfactants, or active components that promote healing (such as oxidised regenerated cellulose, antioxidants or anti-inflammatories).

The oxidoreductase enzyme can be used at a concentration of 0.2 U/mL-60.0 U/mL, preferably at least 1 U/mL, at least 2 U/mL, at least 6 U/ml, at least 10 U/ml or at least 15 U/ml, including 2 U/mL-20 U/mL.

The substrate can be used at a concentration of 10 to 85% w/w, preferably at least 20% w/w, including at least 30% w/w or at least 40% w/w.

The compositions can be used to treat or prevent biofilms formed by any type of pathogenic bacteria. A pathogenic bacteria is a bacteria that is infectious to humans and/or animals. The bacteria can be a Gram-negative bacteria species or a Gram-positive bacteria species. The bacteria can be selected from the group consisting of *Pseudomonas, Staphylococcus, Streptococcus, Salmonella, Escherichia, Klebsiella, Bacillus, Clostridium, Campylobacter, Capnocytophaga, Proteus, Shigella, Bacteroides, Prevotella, Fusobacterium, Aermonas* and *Acinetobacter.*

In a preferred embodiment, the population of bacteria referred to herein comprises or consists of *Pseudomonas aeruginosa*. In a further preferred embodiment, the population of bacteria referred to herein comprises or consists of *Staphylococcus aureus* including methicillin resistant *S. aureus*(MRSA). In a further preferred embodiment, the population of bacteria referred to herein comprises or consists of *Staphylococcus epidermidis*. In a further embodiment, the population of bacteria referred to herein comprises or consists of a combination of *Pseudomonas aeruginosa* and *Staphylococcus aureus*.

Biofilms can form on surface wounds, on medical devices, such as catheters, and on external surfaces, such as hospital vents. The composition disclosed herein can be used to treat biofilms on any type of surface including these surfaces.

The composition disclosed herein can be in any form suitable for applying to one of said surfaces. In a preferred embodiment, the composition is in a form suitable for topical administration, for example, ointment, cream, gel, liquid or in a transdermal patch.

The compositions disclosed herein can, in addition to the substrate and enzyme, comprise or consist of one or more pharmaceutically acceptable carriers. In a preferred embodiment, the carrier is suitable for topical delivery.

The composition can be a liquid, semi-solid or solid composition for application directly to the surface of a wound, or the composition is applied to the surface of, or incorporated into, a solid wound contacting layer such as a wound dressing foam, gauze or film.

Preferably, the wound dressing composition is a fluid or a gel comprising from 0.2 U/mL-60.0 U/mL enzyme and 10 to 85% w/w substrate in combination with one or more conventional pharmaceutical carriers for topical application to a wound.

Suitable carriers include hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (carbopols), creams/ointments used for topical pharmaceutical preparations, e.g. creams based on cetomacrogol emulsifying ointment, a thickener such as alginate, preservatives such as benzyl alcohol, buffers to control pH such as disodium hydrogen phosphate/sodium dihydrogen phosphate, agents to adjust osmolarity such as sodium chloride, purified water and stabilisers such as EDTA.

An embodiment disclosed herein is a composition consisting of glucose oxidase, glucose and a pharmaceutically acceptable carrier for use in treating or preventing biofilm formation in a wound by a population of pathogenic bacteria comprising *Pseudomonas aeruginosa*.

A further embodiment is a composition consisting of glucose oxidase, glucose and a pharmaceutically acceptable carrier for use in treating or preventing biofilm formation in a wound by a population of pathogenic bacteria comprising *Staphylococcus aureus* including methicillin resistant *S. aureus*.

The composition disclosed herein can be administered to the treatment area at least once a day, including twice a day. The treatment can be continued for at least a week, including at least two weeks.

A further aspect relates to a wound dressing comprising a composition disclosed herein for use in treating or preventing biofilm formation by a population of pathogenic bacteria.

The composition disclosed herein can be incorporated into a foam for use as a wound dressing. The wound dressing can be a hydropolymer foam mixture (for example, Tielle®, manufactured by Systagenix), a freeze-dried composite comprising collagen and oxidised regenerated cellulose (for example, Promogran®, manufactured by Systagenix) or a silicone dressing (for example, Adaptic Touch®, manufactured by Systagenix).

The foam may be a reticulated, open-cell polyurethane or polyether foam that allows good permeability of wound fluids. One such foam material that has been used is the V.A.C. Granufoam™ Dressing available from Kinetic Concepts, Inc. (KCI) of San Antonio, Tex. The reticulated pores of the Granufoam™ Dressing material, that are in the range of about 400 to 600 microns. A material with a higher, or lower, density (smaller pore size) than Granufoam™ Dressing material may be desirable in some situations.

The foam material might also be a combination or layering of materials; for example, a first layer of hydrophilic foam might be disposed adjacent to a second layer of hydrophobic foam to form the foam. The foam may also be a reticulated foam that is later felted to a thickness of less about half its original thickness.

The oxidoreductase enzyme and substrate can be incorporated into the wound dressing such that the enzyme and substrate are physically separated from one another. For example, this could be achieved by including the oxidoreductase enzyme in one layer of the dressing and the substrate in another. When the dressing is hydrated, for example by wound exudate, the oxidoreductase enzyme can start metabolising the substrate to produce hydrogen peroxide.

The wound dressing composition in a sheet or layer form could, for example, have an area of from about 1 cm$^2$ to about 400 cm$^2$, in particular from about 2 cm$^2$ to about 100 cm$^2$. The basis weight of the sheet is typically from about 100 g/m$^2$ to about 5000 g/m$^2$, for example from about 400 g/m$^2$ to about 2000 g/m$^2$. The sheet of the composition would form an active layer of the dressing.

The said active layer in the dressings would normally be the wound contacting layer in use, but in some embodiments it could be separated from the wound by a liquid-permeable top sheet. Preferably, the area of the active layer is from about 1 cm$^2$ to about 400 cm$^2$, more preferably from about 4 cm$^2$ to about 100 cm$^2$.

The wound dressing may consist essentially of the active layer of the composition, in which case the dressing would normally be used in conjunction with a suitable secondary dressing. In other embodiments, the wound dressing comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Preferably, the backing sheet is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable.

Suitable polymers for forming the backing sheet include polyurethanes and poly alkoxyalkyl acrylates and methacrylates such as those disclosed in GB-A-1280631.

Preferably, the backing sheet comprises a continuous layer of a high density blocked polyurethane foam that is predominantly closed-cell. The adhesive layer (where present) should be moisture vapour transmitting and/or patterned to allow passage of water vapour therethrough. The adhesive layer is preferably a continuous moisture vapour transmitting, pressure-sensitive adhesive layer of the type conventionally used for island-type wound dressings. Polyurethane-based pressure sensitive adhesives are preferred.

The wound dressing may further comprise an absorbent layer between the active layer and the backing sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof.

A removable cover sheet may protect the wound-facing surface of the dressing. The cover sheet is normally formed from flexible thermoplastic material. Suitable materials include polyesters and polyolefins. Preferably, the adhesive-facing surface of the cover sheet is a release surface. That is to say a surface that is only weakly adherent to the active layer and the adhesive on the backing sheet to assist removal of the cover sheet. For example, the cover sheet may be formed from a non-adherent plastic such as a fluoropolymer, or it may be provided with a release coating such as a silicone or fluoropolymer release coating.

A wound dressing disclosed herein can be used to treating a wide range of wound types where biofilm formation can occur, for example, acute or chronic wounds.

As used herein, the term "wound" means a break in the skin. Examples of wounds include skin ulcers (e.g. bed sores, diabetic ulcers and leg ulcers), burns, surgical wounds and abrasions. Wound may be, for example, chronic, acute, traumatic, sub-acute, dehisced wounds, partial-thickness burns, ulcers (such as diabetic, pressure, or venous insufficiency ulcers), flaps or grafts.

In the case of a chronic wound, the dressing can be applied to the chronic wound for a period of at least 1 hour, at least 6 hours, and at least 12 hours. The treatment may be extended for several days, 1, 2, 3 or more weeks, with dressing changes as appropriate.

The wound can be uninfected, in which case the wound dressing prevents infection. Alternatively, the wound can be infected and the wound dressing treats or reduces the infection by treating biofilm formation.

The composition can be used in conjunction with negative pressure therapy. For example, the composition can be applied directly to a wound that will also be treated with negative pressure therapy or the composition can be incorporated into a wound dressing that is to be used with a vacuum for negative pressure therapy.

The wound dressings will be packaged in sterile packaging, and sterilized using routine methods, such as by gamma-irradiation.

A further aspect relates to an ex vivo or in vivo method of preventing formation of, or removing, a pathogenic bacterial biofilm (that is a biofilm formed by a population of pathogenic bacteria) from a surface comprising administering a composition comprising an oxidoreductase enzyme and a substrate for the enzyme to said surface.

In an ex vivo method, the composition can be used to prevent biofilm formation on a medical device, for example, by coating the medical device in part or completely with the composition prior to use of the device.

A further aspect relates to a method for the treatment or prevention of biofilm formation by a population of pathogenic bacteria, comprising administration of a therapeutic amount of a composition comprising an oxidoreductase enzyme and a substrate to a patient in need thereof.

A further aspect relates to a method for the treatment or prevention of biofilm formation by a population of pathogenic bacteria, comprising administration of a therapeutic amount composition consisting of an oxidoreductase enzyme, a substrate and a pharmaceutically acceptable carrier to a patient in need thereof.

A further aspect relates to a method of treatment or prevention of biofilm formation by a population of pathogenic bacteria in a wound by applying a wound dressing comprising an oxidoreductase enzyme and a substrate to a wound site.

Methods may comprise identifying a wound containing a biofilm, or a wound at risk of infection by biofilm-forming bacteria, and treating the wound by applying the composition of the invention to the wound.

The composition may be applied as a mixture of the oxidoreductase enzyme and substrate, or these two components may be applied separately, e.g., as two solutions. The enzyme and substrate may be administered simultaneously, optionally as a combined preparation, as separate components of a wound dressing, or as a two-part solution.

Compositions of the invention may be incorporated wound dressings as described above. Thus, it may be convenient to apply the composition via a wound dressing, such as a foam or a gauze incorporating the composition. A further aspect relates to a method of manufacturing a composition as disclosed herein. The composition may be manufactured by any suitable processing method. For example, the composition disclosed herein of an oxidoreductase enzyme and a substrate for the enzyme can be mixed with a pharmaceutically acceptable carrier, also as described herein.

Also contemplated is a kit comprising a composition disclosed herein. The kit can include a container comprising the composition and instructions for use of the composition for treating or preventing biofilm formation. The enzyme and substrate may be provided in separate containers and/or separate solutions within the kit.

"Treating" or "preventing" a biofilm, as disclosed herein, refers to reduction or elimination of biofilm from a surface, including killing and/or inhibition of growth of microbes in the biofilm, and/or prophylactic prevention of formation of or growth of a biofilm on a surface.

Treatment or prevention of bacterial biofilms may be determined experimentally as illustrated in the Examples herein. The effect of a composition on a biofilm may be determined by a method including the following steps:
 a) providing a bacterial culture;
 b) inoculating a sterile disc in each of a control and a test culture well with an inoculum from the bacterial culture;
 c) adding the composition to the test culture well;

d) incubating the test and control culture wells under conditions in which the bacteria form a biofilm; and e) determining the number or concentration of bacteria on the discs from the test and control culture wells respectively; wherein a lower number or concentration of bacteria in the test well compared with the control well indicates that the composition is suitable for treating or preventing formation of a biofilm by the bacteria.

Statistical significance of any reduction may be determined. Illustrative methods for the above steps are described in the Examples.

Preferred features of the second and subsequent aspects disclosed herein are as for the first aspect mutatis mutandis.

FIGURES

The present invention will now be further described by way of reference to the following Example and Figures which are provided for the purposes of illustration only and are not to be construed as being limiting on the invention. Reference is made to the following Figures in which.

EXAMPLES

Example 1 Biofilm Model

Method

Figure 1:
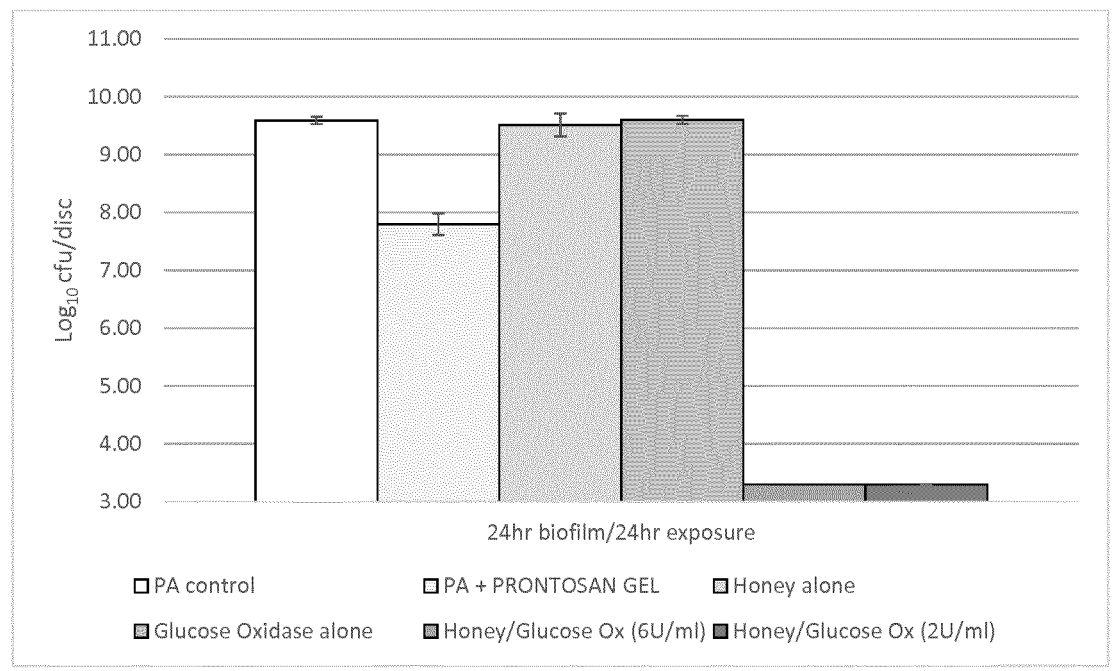
FIG. 1 illustrates the effect of 24 hour honey, glucose oxidase and honey/glucose oxidase exposure against 24 hour old *P. aeruginosa* biofilms.

Stationary phase cultures of *S. aureus* or *P. aeruginosa* grown in TSB were adjusted to 0.5 McFarland (c. $1.5 \times 10^8$ CFU/mL) and diluted a further 1:4 ratio (1 mL inoculum with 3 mL 0.1% Bactopeptone). A viable count was taken of each inoculum preparation. Sterile discs (6 mm diameter× 1.0 mm) housed in 24 well culture plates were inoculated with 80 μL of culture. 0.2 ml of a test media was then added, the assay plates were parafilmed and incubated for 24 h at 37 degrees Celsius with 80 rpm shaking to allow biofilm formation. Unused wells were filled with PBS to increase humidity and prevent evaporation.

After 24 hours incubation, cellulose discs/biofilms were rinsed with PBS to remove any adherent vegetative cells and transferred to 150 μl of fresh media.

For the honey (as the source of glucose) and Prontosan®, 30 μl was added to each test disc.

For the glucose oxidase, a 100 U/ml stock solution was made as follows; glucose oxidase is supplied as 100,000- 250,000 U/g freeze dried powder. Assuming the lowest concentration (100,000 U/g), 3.5 mg (350 U) was added to 3.5 ml of DPBS to give a 100 U/ml working stock which was filter sterilised.

For the *Pseudomonas* experiment, the working stock was diluted in PBS to give a 10 U/ml solution-30 μl was added to a disc/biofilm.

For the *S. aureus* experiment, 100 μl and 300 μl of stock was diluted in 5 ml volumes of PBS to prepare 'low' and 'high' glucose oxidase alone solutions—30 μl added to a disc/biofilm.

For the Honey/Glucose Oxidase Mixture—

Two honey/glucose oxidate mixtures were tested:

A—2 U/g (2 U/ml) referred to as 'Low'—5 g honey+100 μl of glucose oxidase stock (100 U/ml)

B—6 U/g (6 U/ml) referred to as 'High'—5 g honey+300 μl of glucose oxidase stock (300 U/ml)

30 μl of each was added to a disc/biofilm.

The assay plates were parafilmed and incubated for 24 hours at 37° C. with 80 rpm shaking to allow biofilm disruption. Unused wells were filled with PBS to increase humidity and prevent evaporation.

After incubation (with shaking) at 37 degrees, discs/ biofilms were removed and placed in 665 μL DE neutralising broth (1:20 dilution) for 10 mins, vortexed vigorously for 3 minutes then subjected to serial dilution and viable counting onto TSA by Miles and Misra (1:10 serial dilutions, 10 μl spots in triplicate onto agar).

Results

Figure 2:
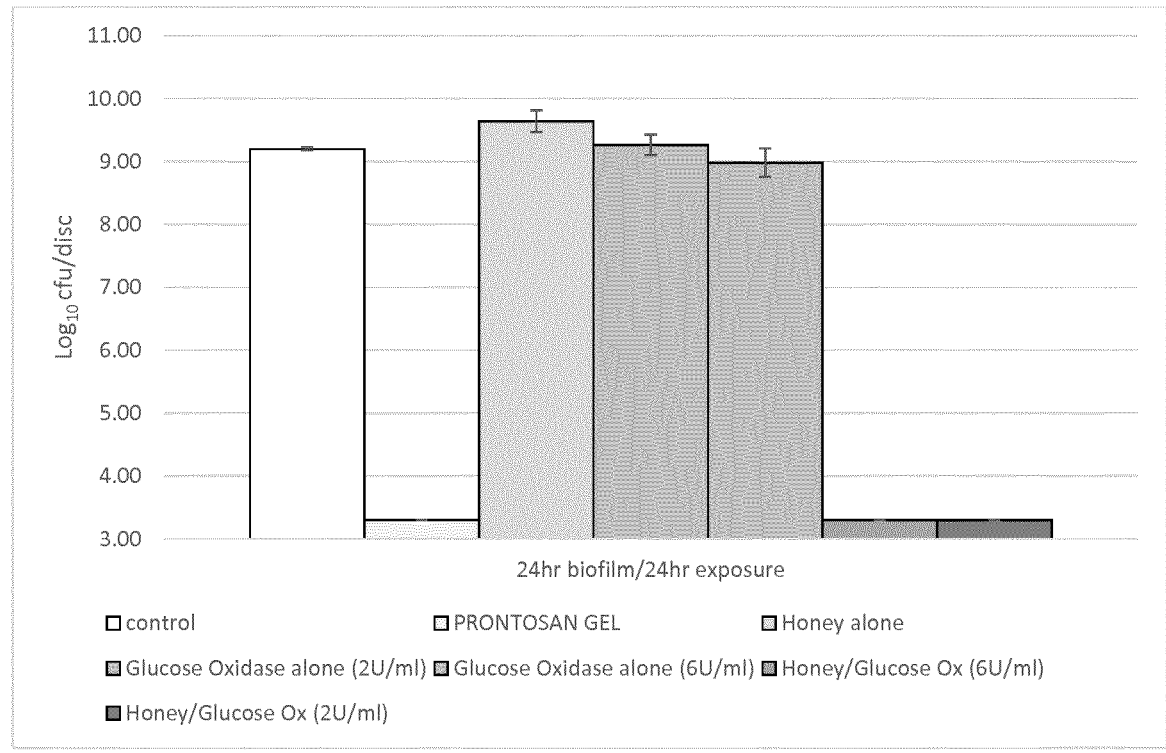
FIG. 2 illustrates the effect of 24 hour honey, glucose oxidase and honey/glucose oxidase exposure against 24 hour old *S. aureus* biofilms.

Both the compositions comprising honey and glucose oxidase demonstrated significant inhibition of 24 hour old single species biofilms of *P. aeruginosa* and *S. aureus*, whereas compositions comprising honey alone and glucose oxidase alone showed no inhibition of the biofilm. Prontosan® gel was highly active against *S. aureus* biofilms but had less activity against *P. aeruginosa* biofilms (see FIGS. 1 and 2).

The invention claimed is:

1. A method for the treatment or prevention of biofilm formation by a population of pathogenic bacteria, comprising administration of a therapeutic amount of a composition comprising an oxidoreductase enzyme and a substrate to a patient in need thereof, wherein the composition does not comprise lactoperoxidase.

2. The method of claim 1, wherein the oxidoreductase enzyme is glucose oxidase and the substrate is glucose.

3. The method of claim 1, wherein the population of pathogenic bacteria comprises *Pseudomonas aeruginosa, Staphylococcus aureus* and/or *Staphylococcus epidermidis*.

4. The method of claim 1, wherein the population of pathogenic bacteria comprises *Pseudomonas aeruginosa*.

5. The method of claim 1, wherein the composition consists of the enzyme, substrate and a pharmaceutically acceptable carrier.

6. The method of claim 1, wherein the composition is administered to a wound on the patient.

7. The method of claim 1, comprising a preceding step of identifying a wound in the patient that contains, or is at risk of infection by, a population of biofilm-forming pathogenic bacteria.

8. The method of claim 7, wherein the wound is a chronic wound.

9. The method of claim 7, further comprising administering negative pressure therapy to the wound.

10. The method of claim 1, wherein the oxidoreductase enzyme in the composition has a concentration of 0.2 U/mL to 60 U/mL.

11. The method of claim 1, wherein the pH of the composition is 4.5-6.5.

* * * * *